(12) United States Patent
Crozet et al.

(10) Patent No.: US 6,375,683 B1
(45) Date of Patent: Apr. 23, 2002

(54) IMPLANT IN PARTICULAR FOR REPLACING A VERTEBRAL BODY IN SURGERY OF THE SPINE

(75) Inventors: Yves Crozet, Seynod; Paolo Mangione, Pessac, both of (FR)

(73) Assignee: Stryker France S.A. (FR)

( * ) Notice: Subject to any disclaimer, the term of this patent is extended or adjusted under 35 U.S.C. 154(b) by 0 days.

(21) Appl. No.: 09/423,173
(22) PCT Filed: Apr. 30, 1998
(86) PCT No.: PCT/FR98/00879
 § 371 Date: Jan. 24, 2000
 § 102(e) Date: Jan. 24, 2000
(87) PCT Pub. No.: WO98/49975
 PCT Pub. Date: Nov. 12, 1998

(30) Foreign Application Priority Data
May 2, 1997 (FR) .............................................. 97 05465

(51) Int. Cl.⁷ .................................................. A61F 2/44
(52) U.S. Cl. .................................................. 623/17.15
(58) Field of Search ........................... 623/17.11, 17.15, 623/17.16

(56) References Cited

U.S. PATENT DOCUMENTS

| | | | |
|---|---|---|---|
| 5,192,327 A | | 3/1993 | Brantigan |
| 5,290,312 A | | 3/1994 | Kojimoto et al. |
| 5,458,641 A | * | 10/1995 | Ramirez Jimenez ..... 623/17.11 |
| 5,522,899 A | | 6/1996 | Michelson |
| 5,653,763 A | * | 8/1997 | Errico ...................... 623/17.11 |
| 5,865,848 A | * | 2/1999 | Baker ....................... 623/17.11 |
| 6,176,882 B1 | * | 1/2001 | Biedermann ............. 623/17.11 |
| 6,190,414 B1 | * | 2/2001 | Young ..................... 623/17.11 |
| 6,193,756 B1 | * | 2/2001 | Studer ..................... 623/17.11 |
| 6,200,348 B1 | * | 3/2001 | Biedermann ............. 623/17.11 |
| 6,214,050 B1 | * | 4/2001 | Huene ..................... 623/17.11 |

FOREIGN PATENT DOCUMENTS

| | | |
|---|---|---|
| FR | 2 636 227 | 3/1990 |
| WO | 97 00054 | 1/1997 |

* cited by examiner

Primary Examiner—Micheal Milano
(74) Attorney, Agent, or Firm—Lerner, David, Littenberg, Krumholz & Mentlik, LLP

(57) ABSTRACT

An implant device designed for replacing a vertebral body of the spine. The implant device contains at least one moving member so as to vary the distance between a first and second member. Most preferably this movement is achieved by rotating at least one cam about an axis. The cam or cams are shaped so as to comprise an irregular polygon thus allowing the height of the implant device to be varied at discrete positions. A slidable telescopic engagement device within the implant device affords the added advantage of simple adjustment and maneuverability.

20 Claims, 5 Drawing Sheets

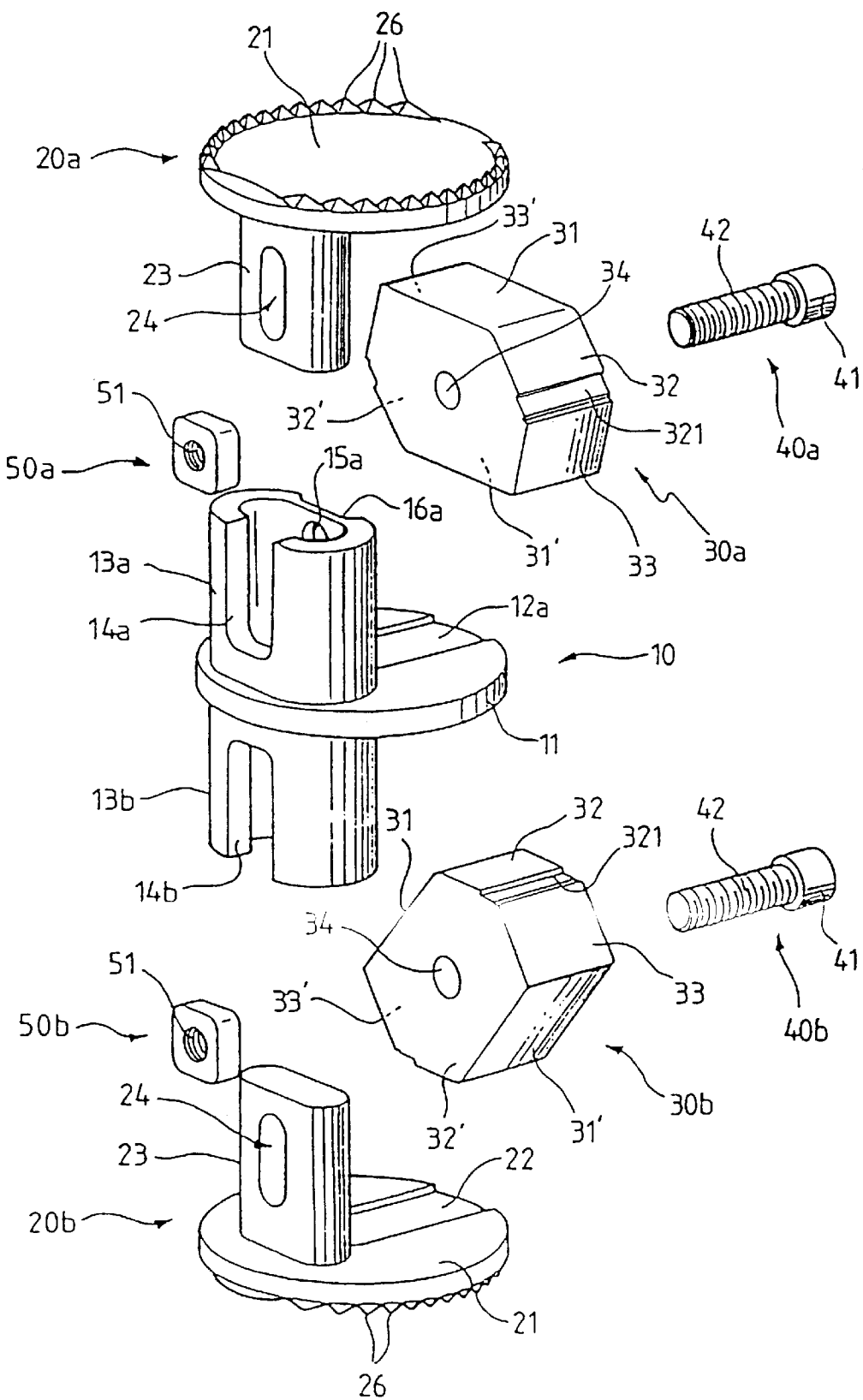

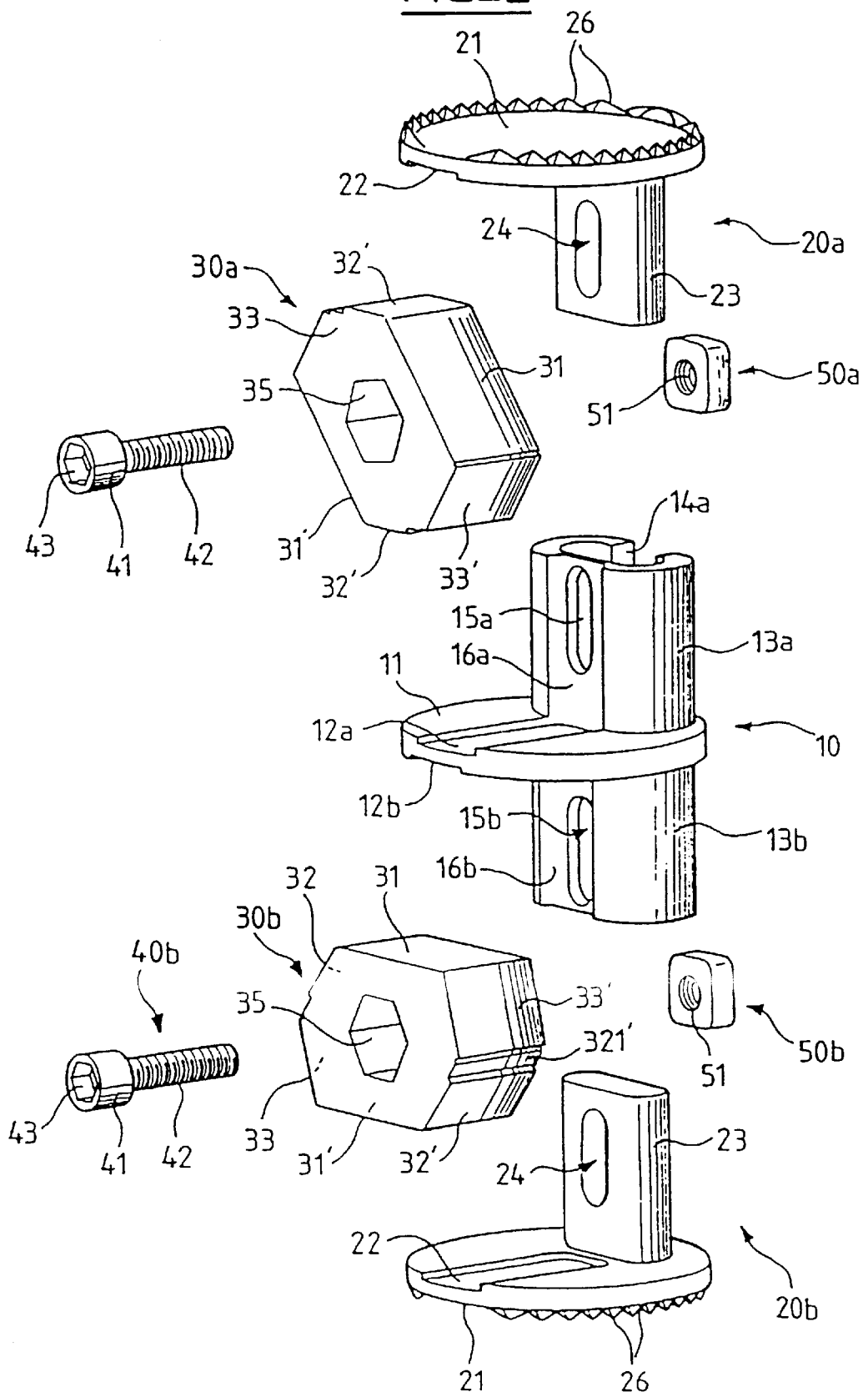

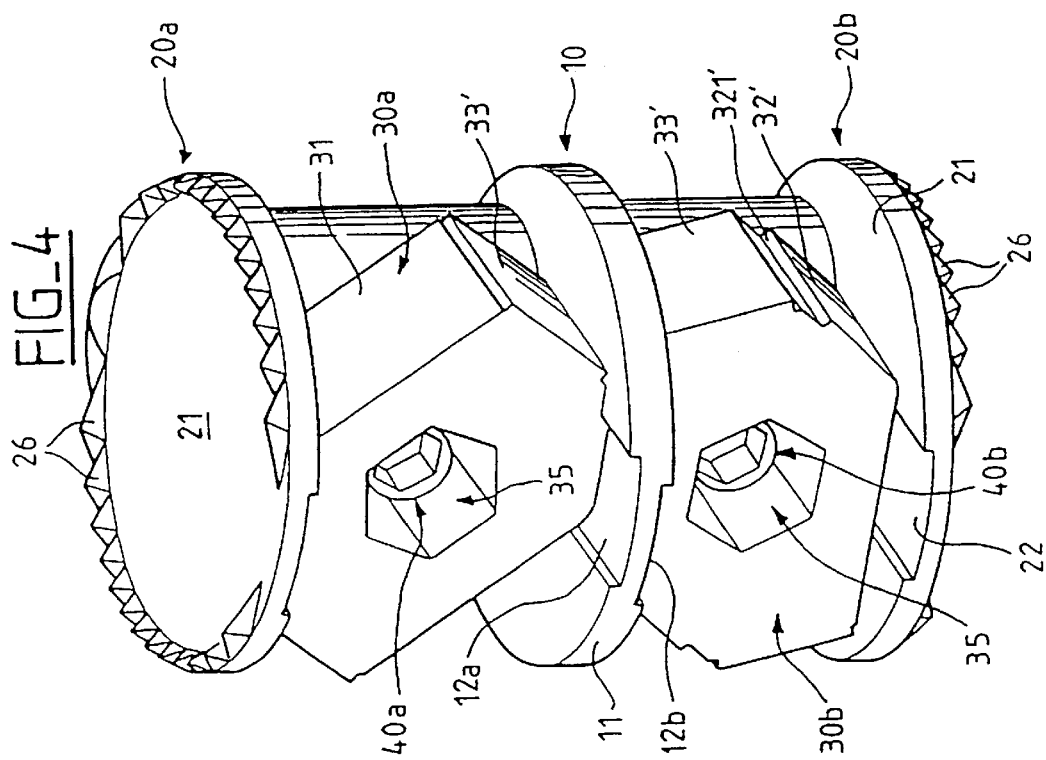
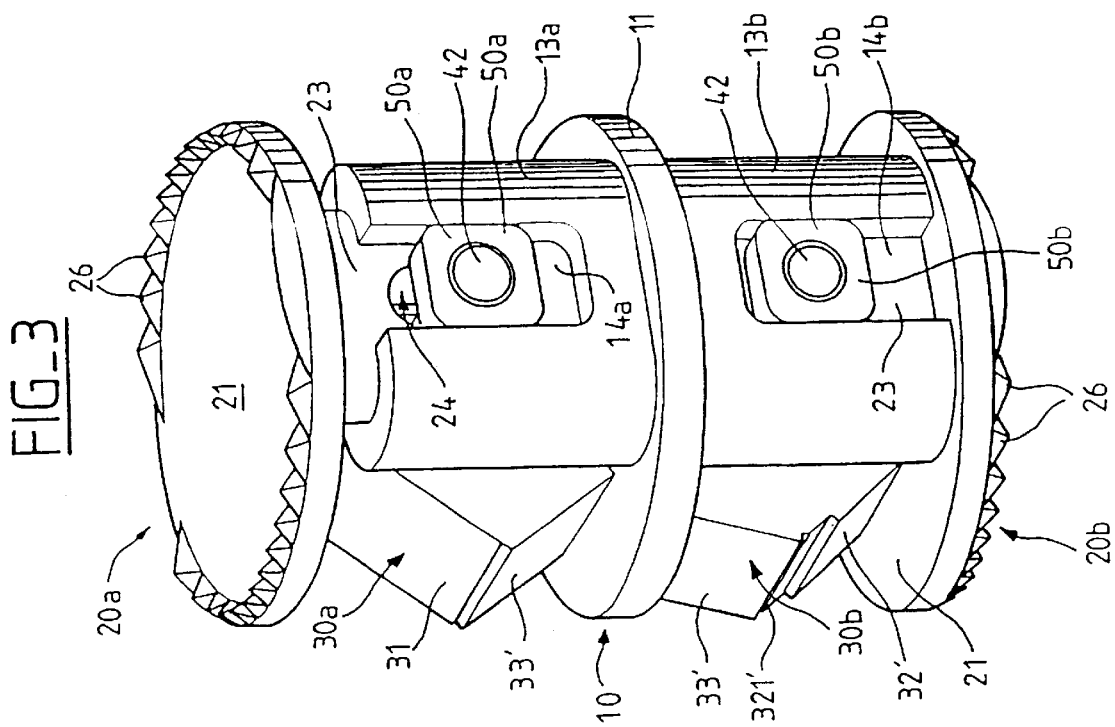

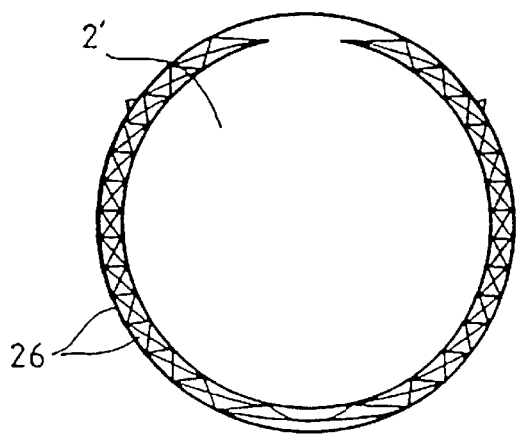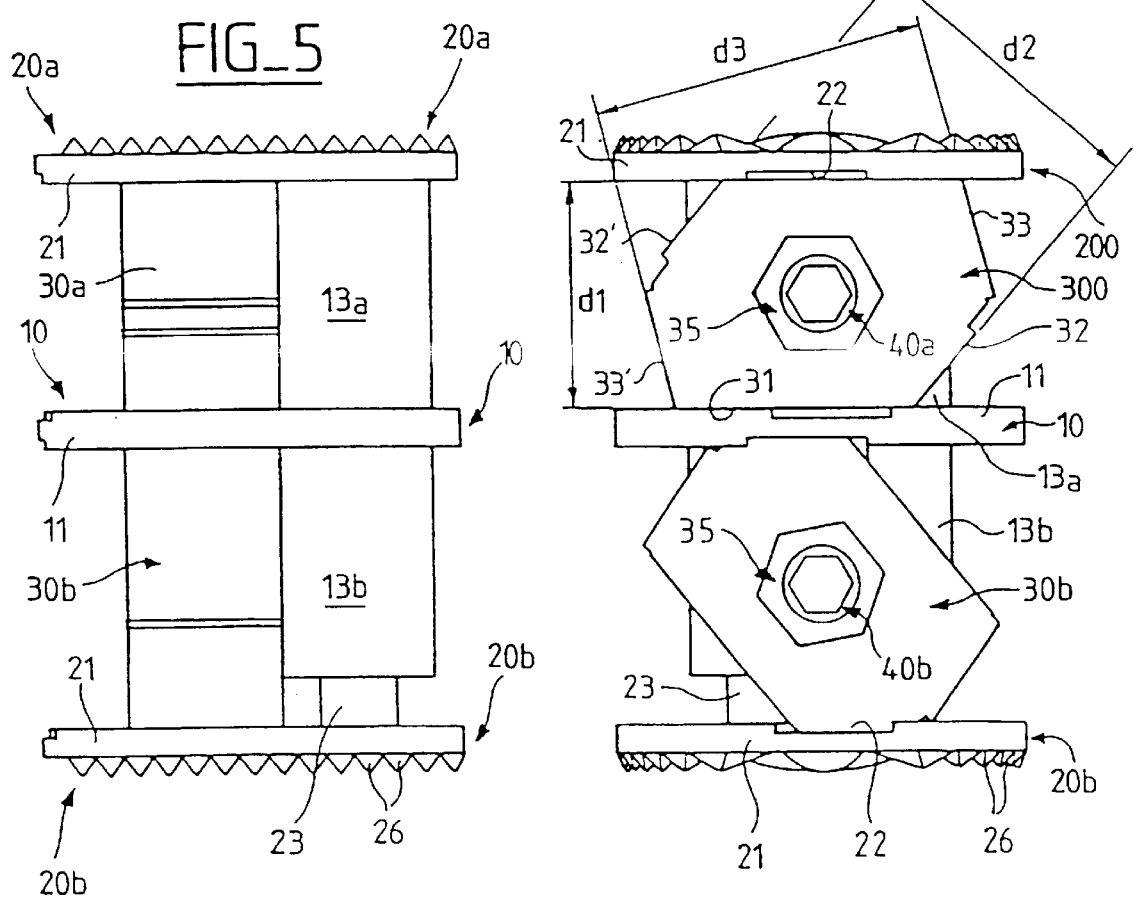

FIG_8
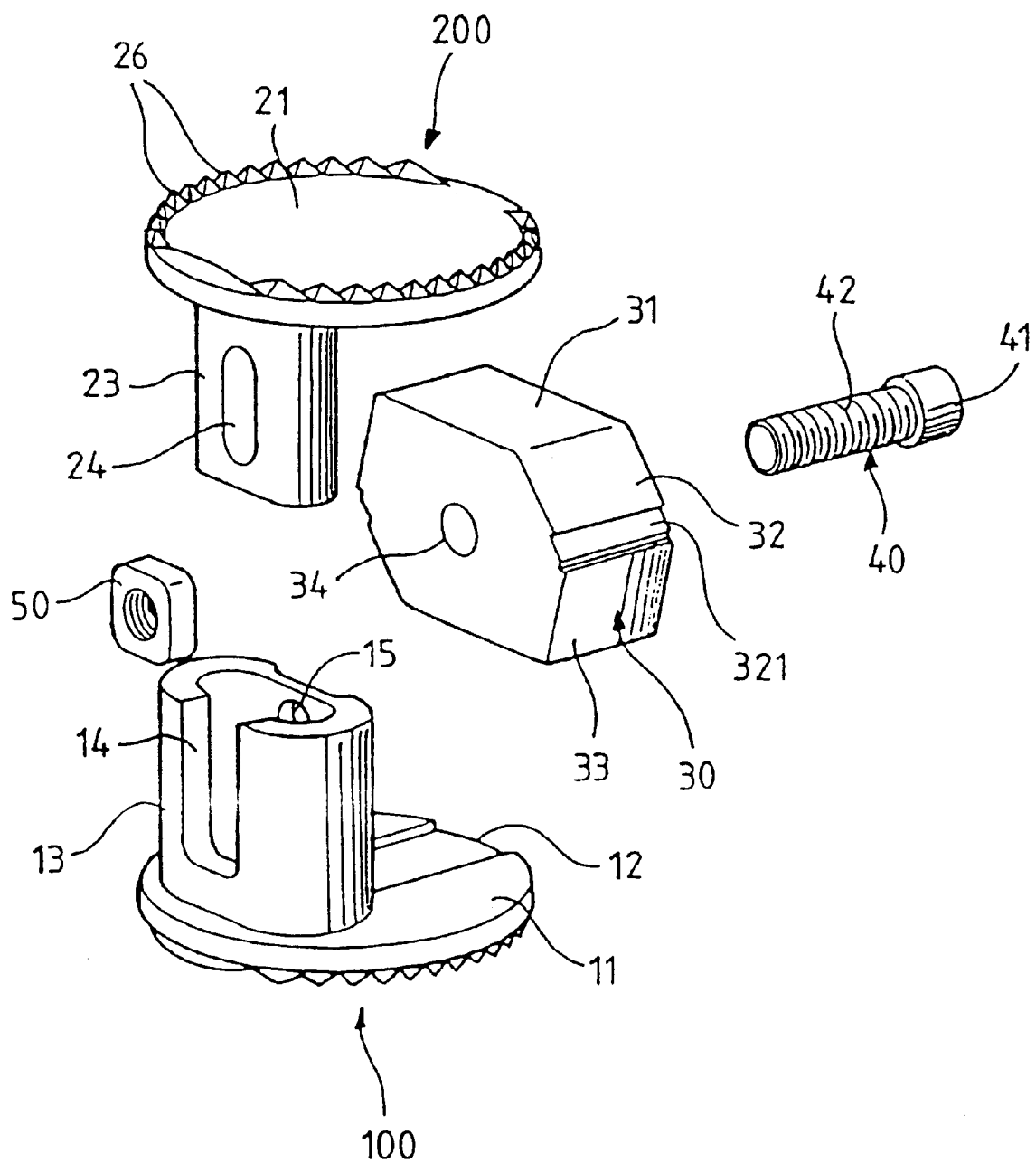

IMPLANT IN PARTICULAR FOR REPLACING A VERTEBRAL BODY IN SURGERY OF THE SPINE

BACKGROUND OF THE INVENTION

Various implants of this type are already known, and conventionally they comprise two elements for bearing against the overlying and underlying vertebral plates, and means for verifying the distance between said bearing elements so as to match the implant to the height required as a function of the morphology of the patient's spine.

The means for varying the height of the implant can comprise a rotary member, together with screw-and-nut type means.

A major drawback of that known implant lies in that the rotary member must be turned about an axis that is substantially parallel to the axis of the spinal column. This can make it extremely difficult to bring the implant to the desired height since the tool used for turning said member, given the surrounding environment of the patient, can be turned through only a small fraction of a complete turn, so it must be maneuvered many times in order to reach the desired height. This is made worse by the fact that the thread must necessarily be fine so as to generate the axial force required for separation purposes without running the risk of producing slip between the bearing elements and the over-and underlying vertebral plates.

The present invention seeks mainly to mitigate that drawback, and to propose an implant for replacing a vertebral body, which implant is simpler to handle when being put into place when performing separation, and which is also provided with excellent stability against the axial compression forces to which it will be exposed.

SUMMARY OF THE INVENTION

Thus, the present invention provides an implant specifically for replacing a vertebral body in surgery of the spine, the implant comprising first and second bearing elements for bearing against under-and overlying vertebral plates, retaining means for retaining the two bearing elements one above the other, and at least one moving member suitable for varying the distance between said bearing elements, the implant being characterized in that the retaining means comprise at least one slideway means provided between the two bearing elements, and in that the or each moving member is constituted by a cam having discrete positions suitable for being rotated about an axis that is essentially horizontal and essentially parallel to the sagittal plane.

Preferred but non-limiting features of the implant of the invention are as follows:

- the or each discrete-position cam has, in cross-section, an outline in the form of an irregular polygon;
- the or each cam possesses a plurality of pairs of faces, the faces in each pair being mutually parallel, and each pair of faces being spaced apart at a distance different from the spacing between the other pairs of faces;
- the cam has three pairs of faces;
- each bearing element possesses a bearing plate having a groove formed in one face thereof, and at least some of the pairs of faces are dimensioned in such a manner as to be of a length in the circumferential direction of the cam that is very slightly shorter than the width of each groove;
- the faces of at least one pair of faces of the cam are of a length, in the circumferential direction of the cam, which is matched to the width of the grooves in the bearing plates by means of respective setbacks provided in transitions between said faces and adjacent faces;
- the or each cam is mounted to move in rotation and in translation on the or each slideway means;
- the or each slideway comprises a hollow slideway-forming upright formed from one element of the implant, and a slider-forming element formed from another element of the implant, and the slideway and the slider have elongate openings passing through them to pass a cam-mounting shaft;
- the cam-mounting shaft is defined by a screw passing through a central passage of the cam and through said elongate openings, and engaged in a nut;
- one of the elongate openings of the slideway is a notch suitable for preventing the nut from rotating;
- the bearing elements have teeth on their outside surfaces for engaging in the vertebrae lying over and under the implant; and
- the implant comprises two bearing elements and a central element, two cams operating respectively between the top bearing element and the central element and between the bottom bearing element and the central element, and two slideway-forming means operating respectively between the top bearing element and the central element and between the bottom bearing element and the central element.

Other aspects, objects, and advantages of the present invention will appear better on reading the following detailed description of a preferred embodiment thereof, given by way of example and made with reference to the accompanying drawings, in which:

BRIEF DESCRIPTION OF THE DRAWINGS

FIGS. 1 and 2 are exploded perspective views of an implant of the invention seen from two different directions;

FIGS. 3 and 4 are perspective views of an implant of the invention in the assembled state, seen from two different directions;

FIG. 5 is an elevation view of the side of the assembled implant of FIGS. 3 and 4;

FIG. 6 is an elevation view of the face of the assembled implant of FIGS. 3 to 5;

FIG. 7 is a plan view of the assembled implant of FIGS. 3 to 6; and

FIG. 8 is an exploded perspective view of a variant embodiment of an implant.

DETAILED DESCRIPTION

With reference to FIGS. 1 to 7, there is shown an implant for replacing a vertebral body, the implant comprising seven elements, namely: a central element 10; two bearing elements 20a and 20b, respectively constituting a top bearing element and a bottom bearing element; two elements forming cams having discrete positions and respectively referenced 30a and 30b, one operating between the element 10 and the element 20a, and the other operating between the element 10 and the element 20b; and finally two screws 40a and 40b suitable for co-operating with two nuts 50a and 50b to hold the assembled implant firmly in the required position.

The central element 10 comprises an intermediate plate 11 that is generally in the form of a horizontal disk. From this disk there extend upwards and downwards respectively a first slideway-forming hollow cylindrical upright 13a, and a second slideway-forming hollow cylindrical upright 13b situated vertically in line with the upright 13a. The section of the slideways 13a and 13b is oval in shape. Each slideway extends from the vicinity of one edge of the disk 11 and has a respective oblong through slot 15a, 15b in its inside face, and has a respective vertically elongate notch 14a, 14b in its outside face, where the notch is slightly wider than the slot and opens out to the free end of the associated slideway.

In addition, each slideway 13a, 13b has a small respective setback 16a, 16b in its inside face, with the oblong slot 15a or 15b passing through the bottom wall of the corresponding setback.

Finally, the central element 10 has a shallow groove 12a of predetermined width in the top face of the disk 11, which groove extends essentially along a diameter of the disk away from the slideway 13a as far as the opposite edge of the disk. An identical and symmetrical groove 12b is formed in the bottom face of the disk 11.

The top element 20a of the implant has a top plate 21 from which there extends downwards a solid slider 23 which is integral with the plate and whose section is slightly smaller than that of the inside section of the slideway 13a, said slider 23 having a slot 24 passing through it of a size that is close to the size of the slot 15a in the element 10.

A series of teeth 26 is formed on the top surface of the plate 21 for reasons explained below, which teeth are more particularly of pyramid shape. Finally, the bottom face of the plate 21 has a groove 22 formed therein of shape and size that are preferably identical to the shape and size of the groove 12a in the central disk 11 of the element 10.

In this case, the bottom element 20b is completely identical to the top element 20a, after merely being turned upside-down through 180°.

The element forming a discrete-position cam referenced 30a for acting between the elements 10 and 20a has an irregular and generally hexagonal outline in cross-section. More precisely, the element 30a possesses:

two mutually parallel opposite large faces 31 and 31' that are spaced apart by an orthogonal distance d1 (see FIG. 6);

two mutually parallel opposite faces 32 and 32' of intermediate size that are spaced apart by an orthogonal distance d2 greater than d1; and two mutually parallel opposite small faces 33 and 33' that are spaced apart by an orthogonal distance d3 greater than d2.

It will also be observed that the transitions between the faces 31 and 33 and between the faces 31' and 33' are slightly rounded.

It will also be observed that the transitions between the faces 32 and 33 and between the faces 32' and 33' are provided with respective setbacks 321 and 321' whose bottoms are parallel to the respective faces 32 and 32' and of depth substantially equal to the depth of the grooves 12a, 12b, and 22 formed respectively in each of the faces of the central disk 11 of the element 10 and in the inside faces of the plates 21 of the elements 20a and 20b.

In addition, the lengths (i.e. dimensions in the circumferential direction) of the various faces of the element 30a are as follows:

the large faces 31 and 31' are of length greater than the width of the grooves 12a, 12b, and 22;

by appropriately selecting the width of the setbacks 321 and 321', the middle faces 32 and 32' are of effective length that is very slightly shorter than the width of the grooves 12a, 12b, and 22; and the small faces 33 and 33' are likewise of an effective length that is very slightly smaller than the width of the grooves 12a, 12b, and 22.

The element 30a also possesses a central through bore 34 which terminates at one of the side faces of the element in an enlarged portion 35 of hexagonal section, forming a socket for receiving a tool as explained below.

In this case, the cam-forming element 30b for operating between the elements 10 and 20b is completely identical to the element 30a.

Finally, the implant of the invention has two identical screws 40a and 40b each possessing a head 41 provided with a socket 43 for a driving tool, and a threaded shank 42, and also has two nuts 50a and 50b of square outline with rounded corners, each having a tapped bore 51 passing therethrough complementary to the thread of the screws.

At this point, it should be observed that:

the cross-section of the sockets 35 is larger than that of the heads 41 of the screws 40a and 40b, while the depth of said sockets 35 is perceptibly greater than the axial dimension of said heads 41;

the outside diameter of the threaded shanks 42 is slightly smaller than the diameter of the bores 34 through the elements 30a and 30b; and the side of each nut 50a and 50b is selected to be slightly smaller than the width of the notches 14a and 14b formed in the uprights 13a and 13b of the element 10;

There follows a description of how the implant of the invention is assembled, and then of the various steps implemented by the surgeon while putting the implant into place.

Firstly, the implant is assembled by inserting the sliders 23 of the elements 20a and 20b in the respective slideways 13a and 13b of the element 10. Thereafter the elements 30a and 30b are prepositioned between the plate 21 of the element 20a and the plate 11, or between the plate 21 of the element 20b and the plate 11, such that the respective bores 34 thereof are in register with the respective slots 15a and 15b. Then the screws 40a and 40b are engaged in the respective passages 35 and 34, in the slots 15a and 15b, and in the notches 14a and 14b where they are screwed into the respective nuts 50a and 50b.

Prior to the implant being put into place, the cam-forming elements 30a and 30b are initially set to their minimum height, i.e. they have their large faces 31 and 31' bearing against the facing faces of the respective plates, projecting on either side of the grooves 12a, 12b, and 22 so as to provide a stable bearing force.

At this stage, the screws 40a and 40b are not tightened, thereby allowing the elements 30a and 30b to be rotated subsequently.

In this minimum-height configuration, the implant is put into place by the surgeon between the vertebral plates of the over-and underlying vertebrae, and if necessary the surgeon performs a small amount of separation to make this possible.

Once the implant has been put into place, a tool is engaged into the sockets 35 of the elements 30a and 30b so as to enable rotation to be imparted thereto, thereby bringing each of these elements:

either into an intermediate position in which the surfaces 32 and 32' bear against the respective plates, and more precisely against the bottoms of the grooves 22 and 12a (or 22 and 12b ); or else in a position of maximum height in which the surfaces 33 and 33' bear against the respective plates, and more precisely, in this case also, against the bottoms of the grooves 22 and 12a (or 22 and 12b).

Since a large amount of torque can be exerted very easily via the posterior access to the elements 30a and 30b, this rotation makes it possible to perform controlled separation between the under-and overlying vertebral plates. The stability of the implant during this separation operation is guaranteed by the teeth 26 of the top and bottom plates 21 which bite into the over-and underlying vertebral plates under the action of the axial force that results from the drive from the cams.

At this point, it will be observed that the presence of two cam-forming elements each having three discrete positions makes it possible to obtain a satisfactory variety of heights for the implant, which heights are given respectively by the following combinations of cam heights:

d1 and d1
d1 and d2
d1 and d3
d2 and d2
d2 and d3
d3 and d3

At this point, it will be observed that by using two elements 30a and 30b of different shapes, the number of combinations can be further increased.

It will also be observed that the surfaces 32 & 32' or 33 & 33' of a cam 30a or 30b being held in the grooves 12a & 22 or 12b & 22 also contributes to the stability of the implant by guaranteeing stability for the angular position of the cam, even in the presence of large compression forces being exerted by the over-and underlying vertebrae, after they have been separated.

The stability of the cam in its position of least height (when the surfaces 31 and 31' are the bearing surfaces) is guaranteed because these surfaces are long.

After the implant has been adjusted to the desired height, the screws 40a and 40b are tightened by means of an appropriate tool to confirm the fixing of the various elements in the required position, the nuts 50a and 50b being blocked against any rotation within the notches 14a and 14b.

FIG. 8 shows a variant embodiment of the invention which can be used when it is desired to obtain an implant of small height.

It differs from the embodiment of FIGS. 1 to 7 in that only one cam-forming element 30 is provided associated with two vertebral thrust elements 100 and 200. The element 100 has a bottom plate 11 provided with teeth 26 on its bottom face and a slideway 13, and with a groove 12 in its top face. The element 200 possesses a top plate 21 provided with teeth 26 on its top face and with a slider 23, and with a groove (not shown) in its bottom face. The cam 30, the screw 40, and the nut 50 are identical to the corresponding elements in the preceding embodiment.

Naturally, the present invention is not limited to the embodiments described and shown, and the person skilled in the art will be able to apply any variant or modification within the spirit of the invention.

What is claimed is:

1. An implant specifically for replacing a vertebral body in surgery of the spine, the implant comprising first and second bearing elements for bearing against under-and overlying vertebral plates, retaining means for retaining the two bearing elements one above the other, and at least one moving member suitable for varying the distance between said bearing elements, the retaining means comprising at least one slideway means provided between the two bearing elements, and in that the or each moving member is constituted by a cam having discrete positions suitable for being rotated about an axis that is essentially horizontal and essentially parallel to the sagittal plane wherein the or each discrete-position cam has, in cross-section, an outline in the form of an irregular polygon.

2. An implant according to claim 1, wherein the or each cam possesses a plurality of pairs of faces, the faces in each pair being mutually parallel, and each pair of faces being spaced apart at a distance (d1, d2, d3) different from the spacing between the other pairs of faces.

3. An implant according to claim 2, wherein the cam has three pairs of faces.

4. An implant according to claim 2 or 4, wherein each bearing element possesses a bearing plate having a groove formed in one face thereof, and in that at least some of the pairs of faces are dimensioned in such a manner as to be of a length in the circumferential direction of the cam that is very slightly shorter than the width of each groove.

5. An implant according to claim 4, wherein the faces of at least one pair of faces of the cam are of a length, in the circumferential direction of the cam, which is matched to the width of the grooves in the bearing plates by means of respective setbacks provided in transitions between said faces and adjacent faces.

6. An implant according to claim 1, wherein the or each cam is mounted to move in rotation and in translation on the or each slideway means.

7. An implant according to claim 6, wherein the or each slideway comprises a hollow slideway-forming upright formed from one element of the implant, and a slider-forming element formed from another element of the implant, and in that the slideway and the slider have elongate openings passing through them to pass a cam-mounting shaft.

8. An implant according to claim 7, wherein the cam-mounting shaft is defined by a screw passing through a central passage of the cam and through said elongate openings, and engaged in a nut.

9. An implant according to claim 8, wherein one of the elongate openings of the slideway is a notch suitable for preventing the nut from rotating.

10. An implant according to claim 1, wherein the bearing elements have teeth on their outside surfaces for engaging in the vertebrae lying over and under the implant.

11. An implant according to claim 1, wherein it comprises two bearing elements and a central element, two cams operating respectively between the top bearing element and the central element and between the bottom bearing element and the central element, and two slidewayforming means operating respectively between the top bearing element and the central element and between the bottom bearing element and the central element.

12. An implant specifically for replacing a vertebral body in surgery of the spine, the implant comprising:

a) a first bearing element and a second bearing element for bearing against underlying and overlying vertebrae;

b) a retainer supporting one of the first bearing element and the second bearing element above the other of the first bearing element and the second bearing element; and c) at least one moving member for varying the distance between said bearing elements;

d) the at least one moving member comprising at least one cam being rotatable about an axis that is essentially horizontal and having discrete positions with respect to the retainer.

13. The implant of claim 12, wherein the retainer has at least one slideway for engaging at least one of the first bearing element and the second bearing element.

14. The implant of claim 12, wherein the at least one cam has a cross-sectional shape, the cross-sectional shape comprising an irregular polygon.

15. The implant of claim 12, wherein the at least one cam has a plurality of pairs of faces, the faces of each pair being mutually parallel.

16. The implant of claim 15, wherein each pair of faces is spaced apart at a distance different from the spacing between the other pairs of faces.

17. The implant of claim 15, wherein the cam has three pairs of faces.

18. The implant of claim 15, wherein each bearing element has a bearing plate with a face, the bearing plate having a groove formed in the face of the bearing plate.

19. The implant of claim 18, wherein at least some of the pairs of faces are dimensioned so that a length in the circumferential direction is slightly shorter than the width of each groove.

20. The implant of claim 19, wherein the faces of at least one of the pairs of faces have a length in the circumferential direction of the cam, the length being matched to the width of the grooves.

* * * * *

UNITED STATES PATENT AND TRADEMARK OFFICE
CERTIFICATE OF CORRECTION

PATENT NO. : 6,375,683 B1
DATED : April 23, 2002
INVENTOR(S) : Crozet et al.

It is certified that error appears in the above-identified patent and that said Letters Patent is hereby corrected as shown below:

Title page, Item [54] and Column 1, line 1,
Title, "IMPLANT IN PARTICULAR" should read -- IMPLANT, IN PARTICULAR --

Column 1,
Line 6, insert the following paragraph
-- The present invention relates in general to implants for surgery of the spine, and more particularly to a novel implant for replacing a vertebral body suffering specifically from a tumor or from a traumatism. --

Column 6,
Line 14, "claim 2 or 4," should read -- claim 2 or 3 --
Line 50, "slidewayforming" should read -- slideway-forming --

Signed and Sealed this

Twenty-fourth Day of September, 2002

Attest:

JAMES E. ROGAN
Attesting Officer
Director of the United States Patent and Trademark Office